United States Patent

Hambitzer et al.

[11] Patent Number: 5,324,938
[45] Date of Patent: Jun. 28, 1994

[54] METHOD AND APPARATUS FOR DETECTING STRIPPABLE SUBSTANCES IN LIQUIDS

[75] Inventors: Günther Hambitzer, Pfinztal; Wolfgang Lutter, Karlsruhe; Martin Joos, Elzach; Ferdinand Hirth, Pfinztal, all of Fed. Rep. of Germany

[73] Assignee: Fraunhofer- Gesellschft zur Forderung der angwandten Forschung e. V., Munich, Fed. Rep. of Germany

[21] Appl. No.: 958,173

[22] Filed: Oct. 8, 1992

[30] Foreign Application Priority Data

Oct. 8, 1991 [DE] Fed. Rep. of Germany ....... 4133300

[51] Int. Cl.[5] .................... B01D 59/44; H01J 49/00
[52] U.S. Cl. ................................. 250/288; 250/282
[58] Field of Search .................... 250/281, 282, 288

[56] References Cited

U.S. PATENT DOCUMENTS

| | | | |
|---|---|---|---|
| 3,943,363 | 3/1976 | Amblerd | 250/288 |
| 4,041,932 | 8/1977 | Fostick | 356/39 |
| 4,757,198 | 7/1988 | Korte et al. | 250/288 |
| 4,810,878 | 3/1989 | Kobayashi | 250/288 |
| 5,024,952 | 6/1991 | Alsop | 210/748 |
| 5,147,561 | 9/1992 | Burge et al. | 210/747 |

FOREIGN PATENT DOCUMENTS 3148312 12/1981 Fed. Rep. of Germany.
4034446 10/1990 Fed. Rep. of Germany.

Primary Examiner—Bruce C. Anderson
Attorney, Agent, or Firm—Antonelli, Terry, Stout & Kraus

[57] ABSTRACT

For the continuous quantitative determination of volatile substances in liquids, such as in particular halogenated hydrocarbons in process or waste waters, the invention proposes a corresponding method, according to which the liquid is led past a liquid-impermeable, but gas-permeable membrane and that the strippable substances in the liquid in their gas phase pass through the membrane and lead same through a measuring cell. An apparatus for performing the method is characterized by a flow chamber provided with a liquid-impermeable, but gas-permeable membrane for the liquids to be investigated and by a measuring cell for the substances to be investigated located on the membrane side remote from the flow chamber.

21 Claims, 3 Drawing Sheets

METHOD AND APPARATUS FOR DETECTING STRIPPABLE SUBSTANCES IN LIQUIDS

TECHNICAL FIELD

The invention relates to a method and an apparatus for detecting strippable substances in liquids, such as in particular halogenated hydrocarbons in process or waste waters.

BACKGROUND ART

The toxicity of cleaning substances in liquids, such as process or waste waters, particularly the toxicity of highly volatile, halogenated hydrocarbons and the increasing damage which they cause to the environment, over the last few years has led to ever lower permitted maximum concentrations for these substances. Therefore for the identification and detection of the substances ever improved detection processes and apparatuses are necessary. At present, the substances are detected by gas chromatography and for this purpose highly developed equipment is required, which is complicated with respect to the mechanical, sensor and electronic means used. For chlorinated hydrocarbons use is also made of halogen-specific flame ionization and electron capture detectors. Furthermore special intake systems are used in combination with the detection processes and it is often necessary to concentrate samples beforehand. As a result of the known methods only discontinuous measurements can be performed on samples. However, in the chemical industry halogenated hydrocarbons are vital key chemicals and must therefore also be continuously measurable in numerous process sequences.

DISCLOSURE OF INVENTION

The problem to which the invention is directed therefore to provide a method and an apparatus for detecting strippable substances from liquids, which also allow a continuous detection of the substances, particularly from flowing liquids and on a real time basis, so that optionally e.g. in the chemical industry, it is possible to carry out control processes with respect to the concentration of certain substances in a liquid.

According to the invention the set problem is solved in a method of the aforementioned type, which is characterized in that the liquid is moved past a liquid-impermeable, but gas-permeable membrane and that the strippable substances in the liquid pass in their gas phase through said membrane and are then guided through a measuring cell. An apparatus for solving the set problem is characterized by a flow chamber for the liquids under investigation which is provided with a liquid-impermeable, but gas-permeable membrane and by a measuring cell for the substances under investigation located on the membrane side remote from the flow chamber.

According to preferred developments of the inventive method the liquid is kept at a constant temperature in the vicinity of the membrane. In this way the flow chamber can be kept at a constant temperature of e.g. 25° C. The pressure transducer should be kept at the same constant temperature as the flow chamber. According to a further development a vacuum is produced on the side of the membrane remote from the liquid, which assists and reinforces the diffusion behaviour of the gaseous substances through the membrane.

According to further improved developments of the inventive method, the liquid fed past the membrane is guided in the branch or secondary branch to the liquid flow to be investigated and that a fraction of the gaseous substances to be investigated is branched off from a region with a limited vacuum, via a pressure transducer with a diaphragm, into a high vacuum branch. According to further development the substances are measured by means of a quadrupole mass spectrometer.

In the apparatus according to the invention the membrane is supported by a porous disk. For the sealing thereof preferably the membrane is sealed by means of a PTFE-enveloped sealing ring in a membrane housing. In order to assist the passage of the substances to be investigated from the liquid through the membrane, according to further developments on the liquid flow chamber is provided with a heating device and/or on the membrane side remote from the flow chamber there is at least one pump in the form of a high vacuum pump.

According to a particularly preferred development the membrane is directly followed by a pump producing a moderate vacuum and that a high vacuum pump is connected by means of a pressure transducer to the flow path of the gas of the first-mentioned pump. If, in accordance with a further development, vacuum measuring cells are present, the vacuum can be kept constant in that said vacuum measuring cells are connected via control loops to the pump or pumps.

To bring a reproducibility of the measured signals and a high constancy of the background signal by description from the walls of the vacuum container, it is advantageous to heat the container to a high temperature of e.g. 80° C.

The liquid from which the substances to be investigated are drawn off through the membrane is preferably passed through a secondary branch. In the apparatus according to the invention a pumping means is provided for pumping the liquid through the flow chamber. To obtain a continuous flow, it is also possible to provide a limited dead volume pressure holder between the pump and the flow chamber. In simple manner a hose clip or a control valve can also be provided.

For increasing the measuring sensitivity of the overall apparatus, according to a preferred development the gas measuring cell is aligned with a diaphragm of the pressure transducer, so that the molecular beam of the substances to be investigated passing through the diaphragm directly strike the measuring cell. The pressure transducer must also be kept at constant temperature and in particular the temperature of the flow chamber.

Preferably, the performing the measurement, the measuring cell has an electron impact ion source of a quadrupole mass spectrometer and the latter has a photomultiplier.

In a specific, preferred development of the invention part of the liquid is sucked from a main flow path or a container by means of a pump and is pumped through a flow chamber of a mass spectrometer provided with a membrane. The flow chamber is heated by means of a heating device, so that the volatile substances to be investigated and optionally a limited water fraction are evaporated and migrate or diffuse through the pores of the porous, hydrophobic membrane into the gas measuring line system. A first stage of a vacuum system is provided here with a diaphragm pump producing a moderate vacuum. By means of a pressure transducer a pressure vacuum system is connected to a corresponding high vacuum pump, so that part of the gas is transferred into the high vacuum and supplied to the mass spectrometric detection system.

BRIEF DESCRIPTION OF THE DRAWINGS

The invention is described in greater detail hereinafter relative to non-limitative embodiments and the attached drawings, wherein show.

BEST MODE FOR CARRYING OUT THE INVENTION

Figure 1:
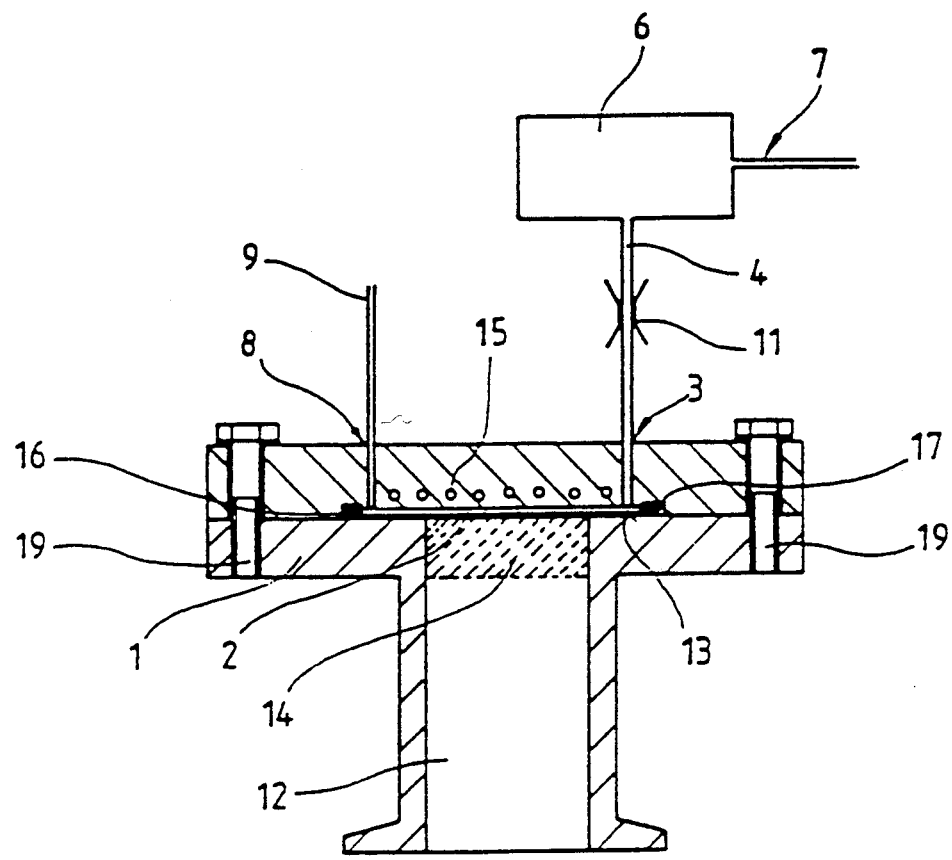
FIG. 1 is a diagrammatic representation of the flow chamber of the present invention.

The apparatus according to the invention has a membrane housing 1 with a flow chamber 2 for the liquid to be tested, checked or investigated. An intake 3 of the flow chamber 2 is connected by means of a line 4 with the outlet of a pump 6, whose inlet is connectable as a branch or secondary branch to a line system carrying the liquid to be investigated or a storage tank containing the liquid to be investigated. An outlet 8 of the flow chamber 2 can be connected by means of a line to a drain or in suitable manner also to the line system, so that the proportion of the liquid to be investigated flowing freely through the flow chamber can be returned to the line system. The lines 4 and 9 are preferably made from high-grade steel and/or a suitable plastics material, such as e.g. Teflon hoses. On the supply line 4 is mounted a hose restriction 11 in the represented embodiment. As a result the pump 6 operates in low-pulsating manner, i.e. with virtually a constant flow rate. Upstream of the hose restriction 11 the pump 6 builds up a pressure of approximately 20 bar when the liquid flows through the flow chamber 2 at approximately atmospheric pressure. When the represented embodiment the flow chamber is located on the pressure side of the pump, it can also be operated on the suction side.

Figure 2:
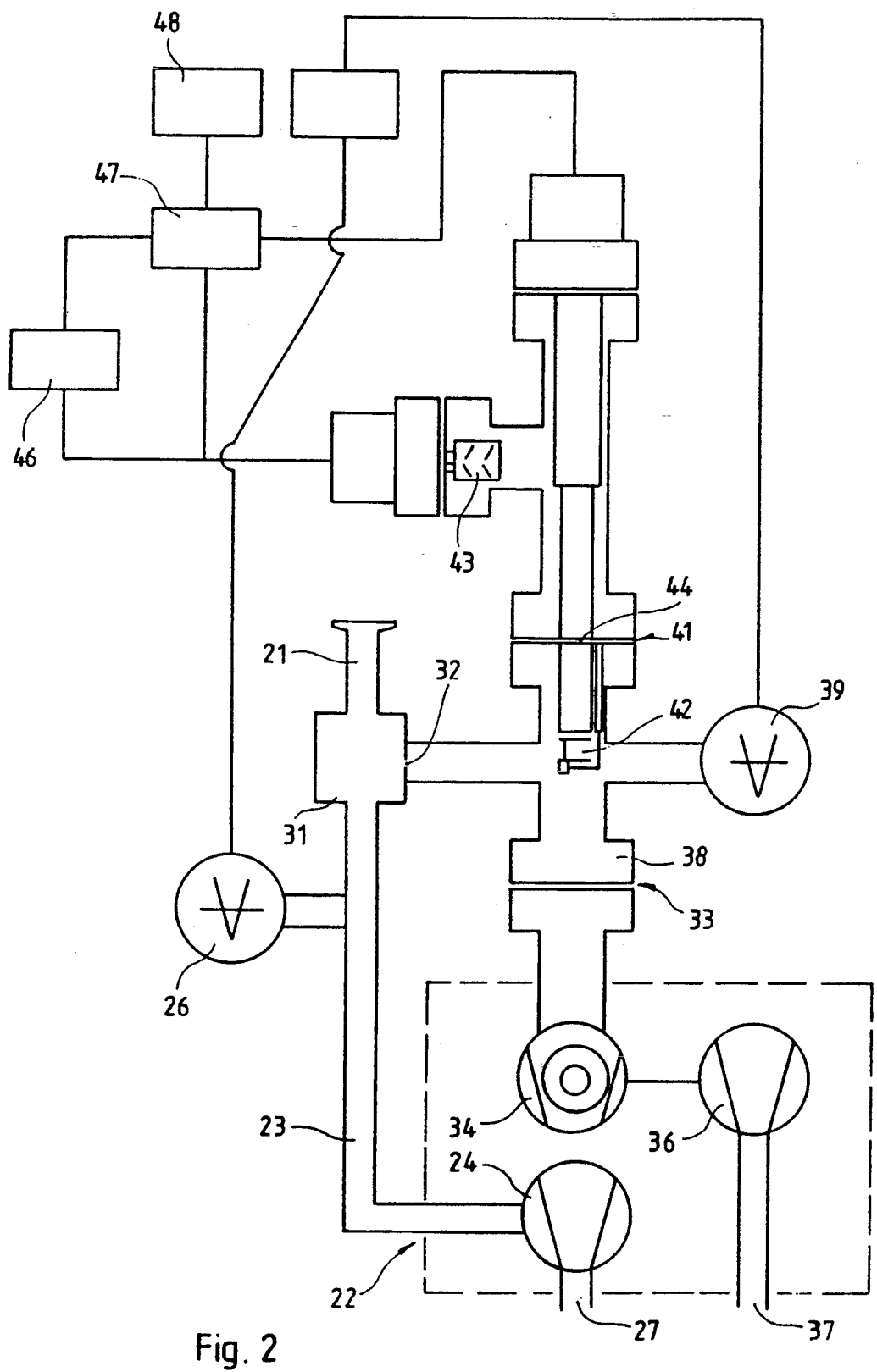
FIG. 2 is a diagramatic representation of the gas side, which is under vacuum, with the vacuum system and measuring device of the present invention.

From the flow chamber 2 a branch 12 leads to the vacuum system as illustrated in FIG. 2. Between the flow chamber 2 and the branch 12 is located a liquid-impermeable, but gas-permeable membrane 13, which is preferably made from PTFE or a copolymer of PTFE and PE, as is marketed under the name Tefzell. The membrane is porous and hydrophobic. It has such a small pore diameter, that at the given liquid pressure, in the present example it is approximately 1 bar, but with decreasing pore size can also be several bars so that no liquid water passes through. The Tefzell membrane used in the example has an average pore radius of 0.05 micrometer, a porosity of 60% and a thickness of 15 micrometers. In order that the membrane does not tear due to the pressure differences between the flow chamber 2 and the vacuum in the connection 12, where the pressure is only a few millibars, it is supported by a porous disk 14. It is preferably a disk such as a steel frit, i.e. containing sintered high-grade steel powder. Preferably it has a porosity of 60% and has pores with a diameter of 50 micrometers. In the represented embodiment the membrane 13 is also sealed by a PTFE-enveloped sealing ring 16 made from fluorocarbon elastomer (Viton ring). The sealing ring is located in a groove 17 of the housing half forming the housing 1 for the flow chamber 2 with the two housing halves being fixed together by screws 19.

In order to obtain short detection response times, all the volumes through which a flow takes place are kept as small as possible. The height in the inner area of the cell is e.g. 0.2 mm. The internal diameter of the metal capillaries and the Teflon boses is 0.7 mm.

The vacuum connection 12 of the membrane housing 1 is connected to the connection 21 of the vacuum system 22. A line 23 to a vacuum pump 24, which produces a moderate vacuum in the millibar range, is connected to the inlet 21. It can be a diaphragm pump, which produces an ultimate vacuum of 1 to 2 millibar (mbar). In the specific embodiment use was made of a diaphragm pump with an ultimate pressure of 1.8 mbar. During operation a pressure of 2.2 mbar was measured with a total pressure gauge 28 provided on the line 23. Such a three-stage vacuum pump with dry working chambers permits a continuous and oil-free pumping of gases. The gases can be pumped by means of the pump 24, via an outlet 27 into the free space, because extremely low concentrations are involved. By means of a pressure transducer 31 with an adjustable diaphragm 32, the connection 21 is also connected to a high vacuum system 33, which has a high vacuum pump 34. The latter is preferably a turbomolecular pump upstream of which is provided a backing pump 36, which can be a diaphragm pump corresponding to the pump 24. The latter is also connected by means of an outlet 37 to the environment. A high vacuum of approximately $10^{-5}$ mbar is produced by the high vacuum pump 34 in the line system 38 leading to it from the pressure transducer 31. The high vacuum pump has an ultimate vacuum of approximately $10^{-10}$ mbar and operates in a substantially oil-free manner. The pressure in the line system 38 can be measured by a high vacuum measuring cell 39. The vacuum measuring cells 26, 39 can be connected in a control loop to the corresponding pumps 27 or 34, 36, so that a constant vacuum is maintained in the line system 38.

The measuring device 41 of the inventive apparatus in the represented embodiment is a quadrupole mass spectrometer. The latter has an electron impact ion source 42, such as a rhenium electron impact ion source, projecting into the line system 38. Said source is followed by a photomultiplier 43 and in the path of the ions from the ion source 42 to the photomultiplier 43 is positioned a quadrupole mass filter 44. The output signal of the photomultiplier 43 is evaluated by a quadrupole/photomultiplier electronics 47, via an electrometer amplifier 46. The measuring parameters can be established by means of a control unit 48. The measurement data can be recorded or outputted by means of a not shown recorder.

Preferably a vacuum container is provided, which receives the sensing probe of the mass spectrometer in such a way that the molecular beam from the diaphragm 32 of the pressure transducer 31 is directed directly onto the ion source 42, as shown in FIG. 2. This reduces the influence of desorption and absorption processes on the walls of the line system 38. The diaphragm has a diamter of 200 micrometers.

The high suction capacity of the vacuum pump 34, preferably a few hundred liters per second, leads to an extremely favourable signal-to-noise ratio, because as a result the intrinsic degassing of the ion source and the desorption from the walls of the line system are kept low and consequently the partial pressure of the background compared with that of the molecular beam fraction remains relatively small.

From a process or waste water line system, which carries process liquids or waste waters containing halogenated hydrocarbons or a vessel containing corresponding liquids, a liquid fraction is pumped by means of the pump 6 through the flow chamber 2, which is preferably provided with a controlled heating means 15. From the liquid fraction flowing through the flow chamber 2, gaseous contaminants contained therein and in particular halogenated hydrocarbons pass through the vacuum at the vacuum connection 10 through the membrane 13 and by means of the porous disk 14, the vacuum connection 12 and the connection 21 (FIG. 2) are sucked by means of the pump 22. The high vacuum pump 34 sucks a fraction of the gases in the line system 23 via the pressure transducer 31 with the diaphragm 32 into the line system 38 and flows past the ion source 42. The resulting suctions gases finally pass out through the outlet 37. The ions produced in the ion source 42, following the mass filter, arrive at the photomultiplier 23 and produce therein a signal corresponding to the mass number or the mass/charge ratio of the contaminant, which, amplified by the electrometer amplifier 46, is evaluated by means of the electronics 47 and outputted or recorded by means of an output unit, such as e.g. a two-channel recorder.

In a specific embodiment of the inventive method chlorinated hydrocarbons, namely chloroform m/2 83 trichloroethylene m/2 95 and methylene chloride m/2 47 were measured for their maximum mass signals in a dilution series of 0.01 to 100 microliters/liter of water. Measurement took place with a pressure in the quadrupole mass filter of $2.5 \times 10^{-5}$ millibar, a photomultiplier amplification of 320 and a flow rate of the liquid of 5 milliliters/minute. For all cases there was a high linearity between the concentration and the associated mass signal over the entire dilution range.

For determining the detection limits in each case solutions were measured with 0.001 microliter/liter of water corresponding in each case to somewhat more than 1 microgram of substance/liter of water. The measured mass signals were clearly above the signal-to-noise ratio, so that there is a detection limit of approximately 1 microgram/liter of water. Using computer-assisted measurement evaluation and further optimization, it should be possible to further lower the detection limit.

Figure 3:
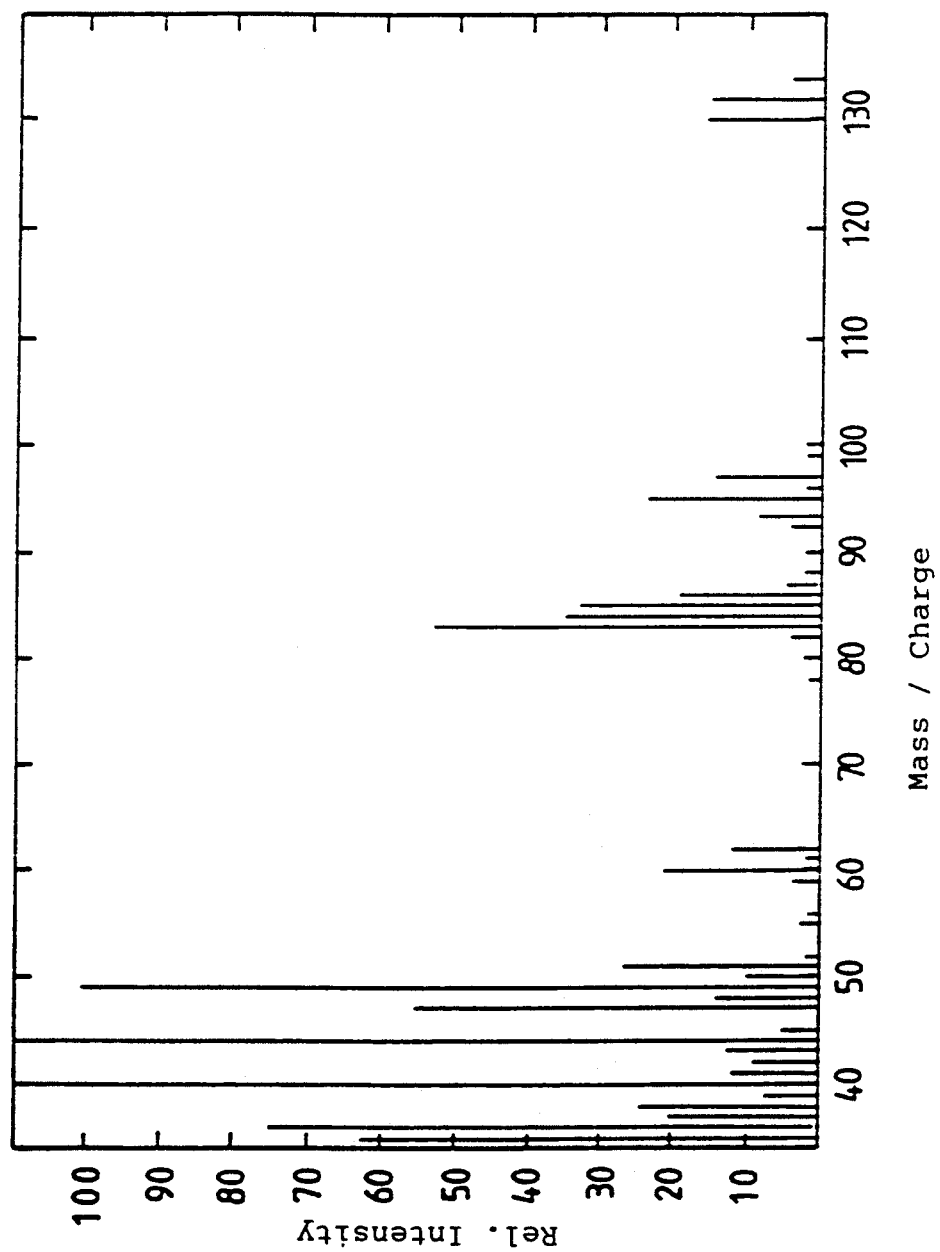
FIG. 3 A measurement result for the mixture of chloroform, trichloroethylene and methylene chloride contained in the water.

For checking the separability of the signals obtained for the individual contaminant substances, a simultaneous determination of said halogenated hydrocarbons was carried out in the form of a mixture with in each case 10 microliters/liter of water. The mass signals obtained are shown in FIG. 3 and it is clearly possible to see the corresponding, relative intensity signals for methylene chloride, chloroform and trichloroethylene in the case of mass/charge numbers of 47, 83.

The measurement was carried out with a mass scan of mass/charge numbers between 35 and 140 and a mass was measured every three seconds. The aforementioned mass parameters were used.

The mass signals can be clearly allocated and therefore each hydrocarbon can be clearly identified. In FIG. 3 the signals at masses 40 and 45 relate to argon or carbon dioxide from the air dissolved in the solution used.

For the scaling of the spectrum the highest peak of the hydrocarbons was chosen as the 100% peak. Therefore argon ($Ar^+$) with a mass/charge ratio (m/z)=40 and carbon dioxide ($Co_2^+$) at m/z=44 are higher. The 100% peak (at m/z=49) is obtained by the addition of the mass signals of two fragment ions, which occur with the same mass/charge ratio, in the form of $CH_2{}^{35}Cl^+$ of methylene chloride and $C^{37}Cl^+$ occurring as the fragment ion in all three hydrocarbons. On the basis of the isotopic ratio and the height of the $C^{35}Cl^+$ peak at 47, it makes a roughly 20% contribution to the overall peak. The $Cl^+$ or $HCl^+$ peaks at m/z± and 37 or 36 and 38 are fragment ions of all three hydrocarbons. The relative proportions are summated. From m/z=83-88 it is alternately possible to see $CHCl_2^+$ (of chloroform) or $CH_2Cl_2^+$ (of methylene chloride). $CHCl_2^+$ occurs at m/z=83 and the isotope peaks of the said fragment ion occur at 85 and 87. $CH_2Cl_2^+$ occurs at m/z=84. The associated isotope peaks are at 86 and 88. Peaks occur through $Re^{2+}$ at m/z=92.5 and 93.5. The electron impact ion source comprises rhenium (Re) and in operation emits continuously decreasing rhenium quantities. At m/z=95 $C_2HCl_2^+$ of trichloroethylene can be seen. The isotope peaks of this fragment ion occur at 97 and 99. The peaks at 130, 132 and 134 also emanate from trichloroethylene and it is possible to see the fragment ion $C_2HCl_3^+$ with a peak at 130 and isotope peaks at 132 and 134. The mass signals at 60 and 62 emanate from the ions $C_2HCl^+$.

Finally the influence of the flow rate on the detection sensitivity was determined. As a result of the evaporation of the highly volatile hydrocarbons at the liquid/gaseous phase boundary (i.e. at the diaphragm) the hydrocarbon constantly diffuses out of the solution. According to laws similar to the channel flow the diffusion distance decreases with increasing flow rate and as a result the mass signal (measured in ampere) rises with the flow rate (milliliter/minute) substantially in the form of a hyperbola.

We claim:

1. A method of measuring strippable substance in a liquid, comprising:
   providing a main flow of the liquid to be tested for presence of strippable substance;
   providing a branch flow from the main flow which flows with surface contact with a liquid impermeable and gas permeable membrane;
   providing a vacuum on a side of the membrane opposed to a side of the membrane having the surface contact with the branch flow of the liquid which draws a gas phase of the strippable substance through the membrane from the branch flow; and
   providing the gas phase to a measuring cell to measure the strippable substance.

2. A method in accordance with claim 1 wherein:
   the strippable substance is a halogenated hydrocarbon contained in water.

3. A method according to claim 1 wherein:
   the liquid is kept at a constant temperature in a vicinity of the membrane.

4. A method according to claims 1 or 3 wherein:
   the vacuum is produced on the side of the membrane opposed to the side of the membrane having surface contact with the branch flow of the liquid.

5. A method according to one of claims 1 or 2 wherein:
   the liquid in surface contact with the membrane is fed back to the main flow of the liquid being investigated.

6. A main flow of the method according to one of claims 1, 3, 4 or 5 wherein:
   a fraction of the gas phase being investigated flows from an area of moderate vacuum via a pressure transducer with a diaphragm to an area of high vacuum.

7. A method according to one of the claims 1 or 3, wherein:
   the strippable substances are measured by means of a mass spectrometer.

8. An apparatus according to claim 3 further comprising:
   at least one pump disposed on a side of the membrane opposed to the side of the membrane having surface contact with the branch flow of the liquid through the flow chamber.

9. An apparatus according to claim 8 wherein:
   the at least one pump is a vacuum pump.

10. An apparatus for measuring a strippable substance in a liquid comprising:
    a flow chamber coupled to and in fluid communication with a branch line for connection to a main flow of liquid to be tested for the strippable substance;
    a liquid impermeable and gas permeable membrane disposed in a side wall of the flow chamber and being in surface contact with the liquid when the liquid flows through the flow chamber;
    a branch pipe joined to the flow chamber, in fluid communication with a side of the membrane opposed to a side of the membrane in surface contact with the liquid when liquid flows through the flow chamber, for receiving a gaseous phase of the strippable substance passing through the membrane from the liquid being tested and conveying the gaseous phase to a gas measuring cell for measuring the strippable substance; and
    a vacuum pump coupled to the branch pipe for drawing the gaseous phase from the liquid being tested through the membrane and the branch pipe into contact with the measuring cell.

11. An apparatus according to claim 10 wherein:
    the membrane is supported by a porous disk.

12. An apparatus according to claim 10 wherein:
    the membrane is sealed in a membrane housing by a PTFE-enveloped sealing ring.

13. An apparatus according to claim 10 wherein:
    a controlled heating device is located at the flow chamber.

14. An apparatus according to claim 10 further comprising:
    a pump for pumping the liquid through the flow chamber.

15. An apparatus according to claim 14 further comprising:
    a restriction is provided between the pump and the flow chamber.

16. An apparatus according to claim 10 wherein:
    the membrane is directly coupled to a pump producing a moderate vacuum and the moderate vacuum pump is coupled to a high vacuum pump connected by means of a pressure transducer to a flow path of the gas from the pump producing a moderate vacuum.

17. An apparatus according to claim 16 further comprising:
    a vacuum measuring cell coupled to each pump.

18. An apparatus according to claim 17 wherein:
    the vacuum measuring cells are connected by control loops to the at least one pump.

19. An apparatus according to claim 10 wherein:
    the gas measuring cell is aligned with a membrane of a pressure transducer for receiving a molecular beam of the strippable substances to be measured passing through the diaphragm and directly striking the measuring cell.

20. An apparatus according to claim 10 wherein:
    the gas measuring cell has an electron impact ion source provided by a quadrupole mass spectrometer.

21. An apparatus according to claim 20 wherein:
    the quadrupole mass spectrometer has a photomultiplier.

* * * * *